(12) United States Patent
Hsu et al.

(10) Patent No.: US 8,905,929 B2
(45) Date of Patent: Dec. 9, 2014

(54) REMOTE SLEEP QUALITY DETECTING METHOD

(71) Applicant: Yuan Ze University, Taoyuan County (TW)

(72) Inventors: Yeh-Liang Hsu, Taoyuan County (TW); Chih-Ming Cheng, Taipei County (TW)

(73) Assignee: Yuan Ze University, Taoyuan County (TW)

( * ) Notice: Subject to any disclaimer, the term of this patent is extended or adjusted under 35 U.S.C. 154(b) by 55 days.

(21) Appl. No.: 13/712,376

(22) Filed: Dec. 12, 2012

(65) Prior Publication Data

US 2013/0102931 A1    Apr. 25, 2013

Related U.S. Application Data

(62) Division of application No. 12/573,226, filed on Oct. 5, 2009, now Pat. No. 8,353,828.

(51) Int. Cl.
*A61B 5/00* (2006.01)
*A61B 5/11* (2006.01)
*G06F 19/00* (2011.01)
*A61N 1/36* (2006.01)
*A61N 1/372* (2006.01)

(52) U.S. Cl.
CPC .............. *A61B 5/4815* (2013.01); *A61B 5/1118* (2013.01); *A61B 5/0004* (2013.01); *A61N 1/36014* (2013.01); *G06F 19/3418* (2013.01); *A61B 5/11* (2013.01); *A61B 5/7225* (2013.01); *A61B 5/7203* (2013.01); *A61B 5/746* (2013.01); *A61N 1/37247* (2013.01)
USPC ........................................................ 600/301

(58) Field of Classification Search
None
See application file for complete search history.

(56) References Cited

U.S. PATENT DOCUMENTS 5,295,490 A * 3/1994 Dodakian ...................... 600/534
6,491,647 B1 * 12/2002 Bridger et al. ................. 600/585
7,491,181 B2 * 2/2009 Heruth et al. .................. 600/595

* cited by examiner

*Primary Examiner* — Brian T Gedeon
(74) *Attorney, Agent, or Firm* — Houtteman Law LLC

(57) ABSTRACT

A remote sleep quality detecting system and its method provide a portable detecting device for detecting an examinee's physical activity while the examinee is sleeping, analyzing a detected activity signal by a signal processing module to generate a statistical value, and comparing a result of the computed statistical value with a sleep state index to obtain sleep quality information, and then storing the activity signal and the sleep quality information in a storage unit. The system and method also provide a remote monitoring device including a sleep information reading module for providing a user interface, connecting the portable detecting device via the Internet and receiving the sleep quality information produced by the portable detecting device after a command from the portable detecting device is received, such that the examinee's sleep quality information can be examined from a remote location for a long term without disturbing the examinee's sleep.

7 Claims, 10 Drawing Sheets

REMOTE SLEEP QUALITY DETECTING METHOD

BACKGROUND OF THE INVENTION

1. Field of the Invention

The present invention relates to a remote sleep quality detecting system and a method thereof, and more particularly to a distributed remote sleep quality detecting system and a method thereof.

2. Description of Related Art

As pressure and tiredness are imposed on our work and daily life, many people have sleep disorder symptoms and need a professional medical treatment system for curing their sleep disorder. Physical activity information of a patient are collected while the patient is sleeping and used as a basis for determining the cause of the sleep disorder and performing a diagnosis to prevent a severer condition of the sleep disorder such as Obstructive Sleep Apnea Syndrome (OSAS) that may cause daytime sleepiness, chest pain, and myocardial infarction, or even become fatal in a serious case. Therefore, the frequency and the interval of snores measured while a patient is sleeping can be used for determining whether or not there is a probability of OSAS, so as to provide an early treatment to patients.

Most present sleep disorder detection systems are installed in hospitals or clinics, and special sleep centers are established in hospitals and clinics for detecting sleep information. In general, an examinee has to go to a specific location of the sleeping center to take a test. In the test, electrode tabs or detection circuits are attached onto the examinee's body, and the examinee sleeps in the center and allows instruments to read data including brain wave, breathing or hemoglobin concentration which are provided for medical professionals to evaluate and diagnose the examinee's sleep condition.

Since the examinee has to take the test in an unfamiliar environment and attach the detection circuits on her/his body, it may increase the examinee's psychological pressure before the examinee falls asleep, and thus resulting in an abnormal sleep condition, and causing a misjudgment on the diagnosis of a patient's sleep disorder.

In the situation of having increasingly more patients who require a sleeping test and need medical treatment for their sleep disorder problem, it is an important subject to let examinees take the sleep quality test at ease in a familiar environment and also allow medical professionals to control the examinee's sleep information for an accurate analysis.

SUMMARY OF THE INVENTION

Therefore, it is a primary objective of the present invention to overcome the shortcomings of the prior art by providing a remote sleep quality detecting system to achieve the effect of detecting an examinee's sleep information in a familiar sleep environment conveniently.

To achieve the foregoing objective, the present invention provides a remote sleep quality detecting system comprising a portable detecting device and a remote monitoring device. The portable detecting device comprises at least one signal detector, a signal processing module, a storage unit and a network transmission unit, wherein the signal processing module further comprises an analysis module and a computation module, and the remote monitoring device further comprises a sleep quality reading module.

The signal detector detects the examinee's physical activity while the examinee is sleeping and generates an activity signal. The analysis module analyzes changes of the activity signal, performs a classification and collect statistics according to the variation of the activity signal, produces a statistical value required for a computation by the computation module, and compares a computed result with at least one sleep state index by a computation module to produce sleep quality information, transmit the sleep quality information from the network transmission unit to a network, and record and store the activity signal and the sleep quality information in the storage unit.

The remote monitoring device monitors the sleep quality information via the network, and the sleep quality reading module installed in the device provides a user interface for receiving a connection instruction to connect a portable detecting device, reading the sleep quality information stored in the storage unit, and displaying the sleep quality information on the user interface.

The sleep quality information can be obtained from a remote location without disturbing the examinee, and the results can be observed for a long term and provided for further analyses.

To achieve the foregoing objective, the present invention provides a remote sleep quality detecting method, comprising the steps of: providing a signal detector for continuously detecting the examinee's physical activity while the examinee is sleeping and generating an activity signal; analyzing changes of the activity signal, and classifying and collecting statistics of the activity signal according to its variation, and producing a statistical value; comparing a computation result obtained after the statistical value is computed with at least one sleep state index to produce sleep quality information, and storing the sleep quality information in a storage unit; and finally providing a remote monitoring device for connecting a network, and reading and displaying the sleep quality information on a user interface.

Therefore, the examinee's sleep information can be observed and recorded from a remote location for a long term without affecting the examinee's sleeping habits, and the sleep information obtained from the method can serve as a basis for a professional medical system to perform further evaluations.

The above and other objects, features and advantages of the present invention will become apparent from the following detailed description taken with the accompanying drawings.

DETAILED DESCRIPTION OF THE PREFERRED EMBODIMENTS

The present invention discloses a remote sleep quality detecting system and its method that provide a way or receiving a sleep quality detection of an examinee in a familiar natural sleeping environment without disturbing the examinee's sleeping habits. In the meantime, medical professionals can control the examinee's sleep quality information from a remote location via a network to achieve the effects of monitoring the examinee's sleep quality information for a long term, eliminating the discomfort during the examinee's sleep quality detection, and lowering the cost of detecting the sleep quality information.

To make it easier for our examiner to understand the technical characteristics of the present invention, we use preferred embodiments together with related block diagrams and flow charts for the detailed description of the invention as follows.

Figure 1:
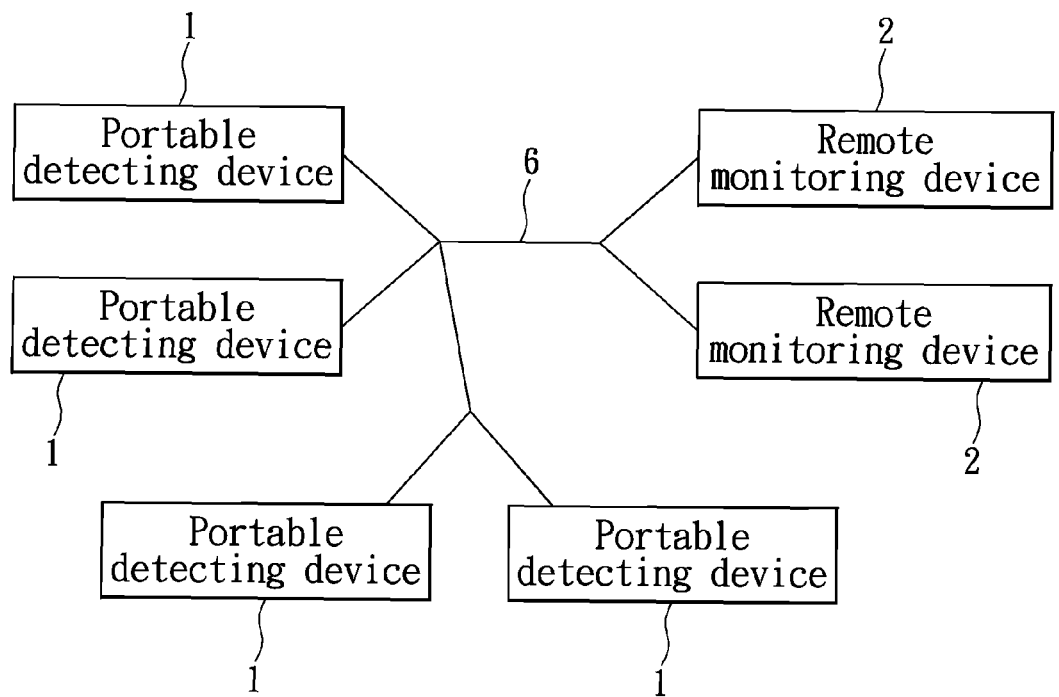
FIG. 1 shows a structure of a sleep quality detection system in accordance with the present invention.

With reference to FIG. 1 for a schematic view of a structure of a sleep quality detection system in accordance with the present invention, the remote sleep quality detecting system in this embodiment is a distributed structure that allows a portable detecting device 1 at the location of the examinee and a remote monitoring device 2 at the location of a medical and healthcare professional to be connected with each other through a network 6, so as to waive the installation of a central server. The remote monitoring device 2 with a monitoring priority can be connected to obtain information recorded in the portable detecting device 1 anytime when needed to facilitate medical and healthcare professionals to control the examinee's sleep quality information.

Figure 2:
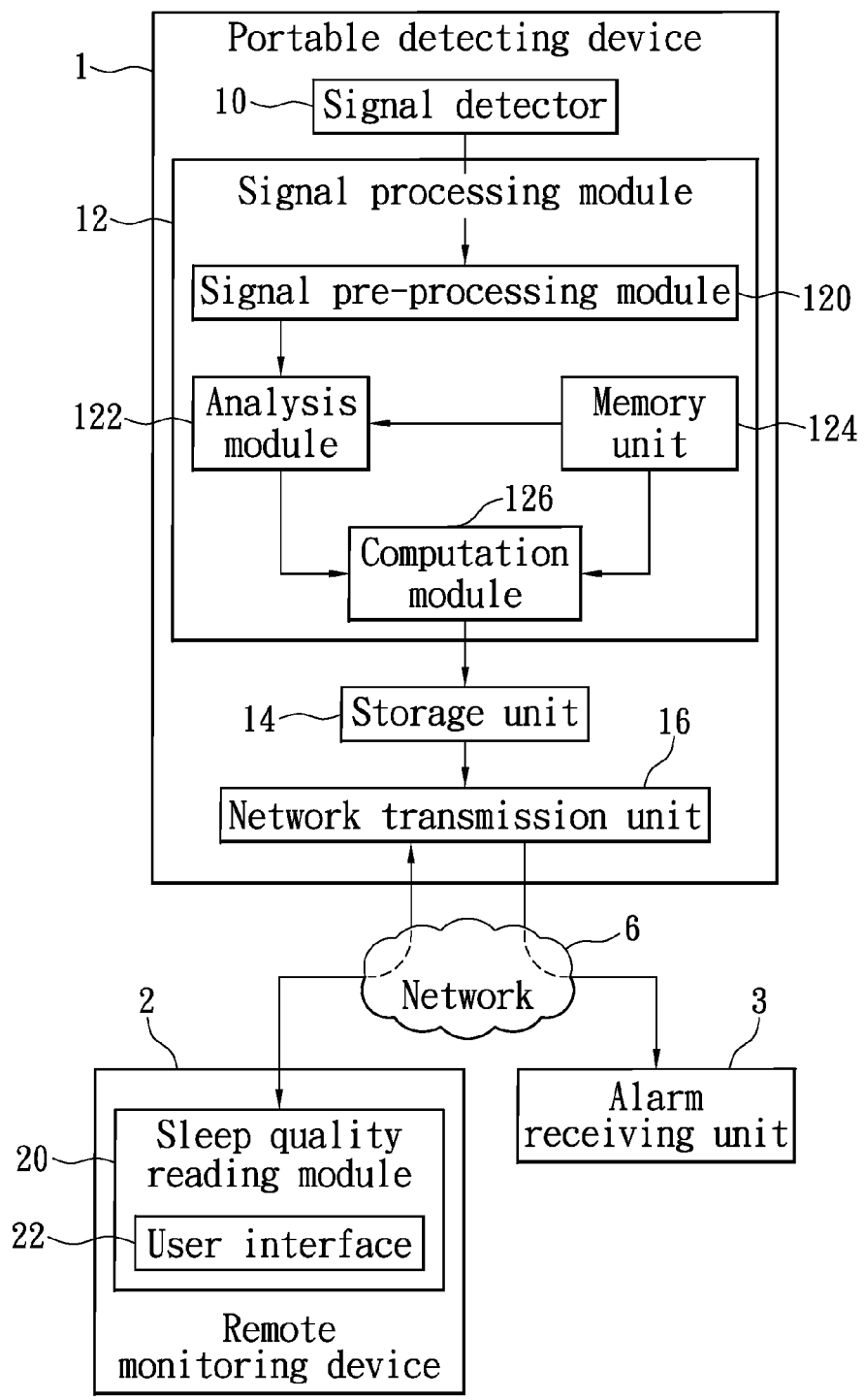
FIG. 2 is a block diagram of a sleep quality detection system in accordance with a preferred embodiment of the present invention.

With reference to FIG. 2 for a block diagram of a remote sleep quality detecting system in accordance with a preferred embodiment of the present invention, the system comprises a portable detecting device 1, a remote monitoring device 2 and an alarm receiving unit 3. The portable detecting device 1 comprises a signal detector 10, a signal processing module 12, a storage unit 14 and a network transmission unit 16. The remote monitoring device 2 comprises a sleep quality reading module 20, and a sleep quality reading module 20 provides a user interface 22.

The signal detector 10 is provided for detecting physical activity such as body turnover, limb swinging, or a breathing sound of the examinee while the examinee is sleeping, generating an activity signal according to the physical activity, and transmitting the activity signal to the signal processing module 12. A signal pre-processing module 120 in the signal processing module 12 converts the analog activity signal into a digital signal and filters noises in the digital signal to provide a smoother waveform of the signal, while sampling the signals per unit time and facilitate analyzing and computing the activity signal.

The activity signal received and analyzed by the analysis module 122 and processed by the signal pre-processing module 120 varies with time, such as the variation of the slope of the activity signal's waveform. The variation can be used for collecting and classifying statistics of the activity signal to produce a statistical value. The computation module 126 computes the statistical value and compares the computed result with at least one sleep state index to produce sleep quality information. The memory unit 124 records a variation threshold, at least one computation equation and the aforementioned sleep state index, and the analysis module 122 classifies the activity signal according to the variation threshold, and the computation module 126 reads the computation equation to compute the statistical value. The produced sleep quality information is transmitted to a network 6 through a network transmission unit 16.

The information monitored by the remote monitoring device 2 is the aforementioned sleep quality information, and the remote monitoring device 2 comprises a sleep quality reading module 20 for providing a user interface 22, and the user interface 22 receives a connection instruction of the portable detecting device 1, such as receiving a network address of the portable detecting device 1, connecting to the portable detecting device 1 via the network 6, timely reading history information stored in the sleep quality information or storage unit 14 according to the monitoring requirement, and displaying the history information on the user interface 22.

If the portable detecting device 1 detects an abnormal activity signal of the examinee such as continuous swings of limbs or an abnormal interrupt of sound signals, then the network transmission unit 16 will send an alarm notice to an alarm receiving unit 3 such as a mobile communication device or an email, so that medical and healthcare professionals can handle the emergency situation immediately upon the receipt of the alarm notice.

With the use of the foregoing system, the examinee can carry the portable detecting device 1 home, and detect the activity signal in a sleeping environment familiar to the examinee without the need of taking the test at a sleep center of a hospital or a clinic, so that medical and healthcare professionals can monitor the sleep quality information of the examinee who is using a portable detecting device 1 from a remote location via the network 6 anytime, without interrupting the examinee's sleep. Since the examinee's activity signal stored in the storage unit 14 is computed to produce sleep quality information, therefore, the effect of observing the examinee's sleep condition for a long term can be achieved to reduce the examinee's psychological pressure of taking the test in a sleeping center and lower the cost of medical care.

Figure 3:
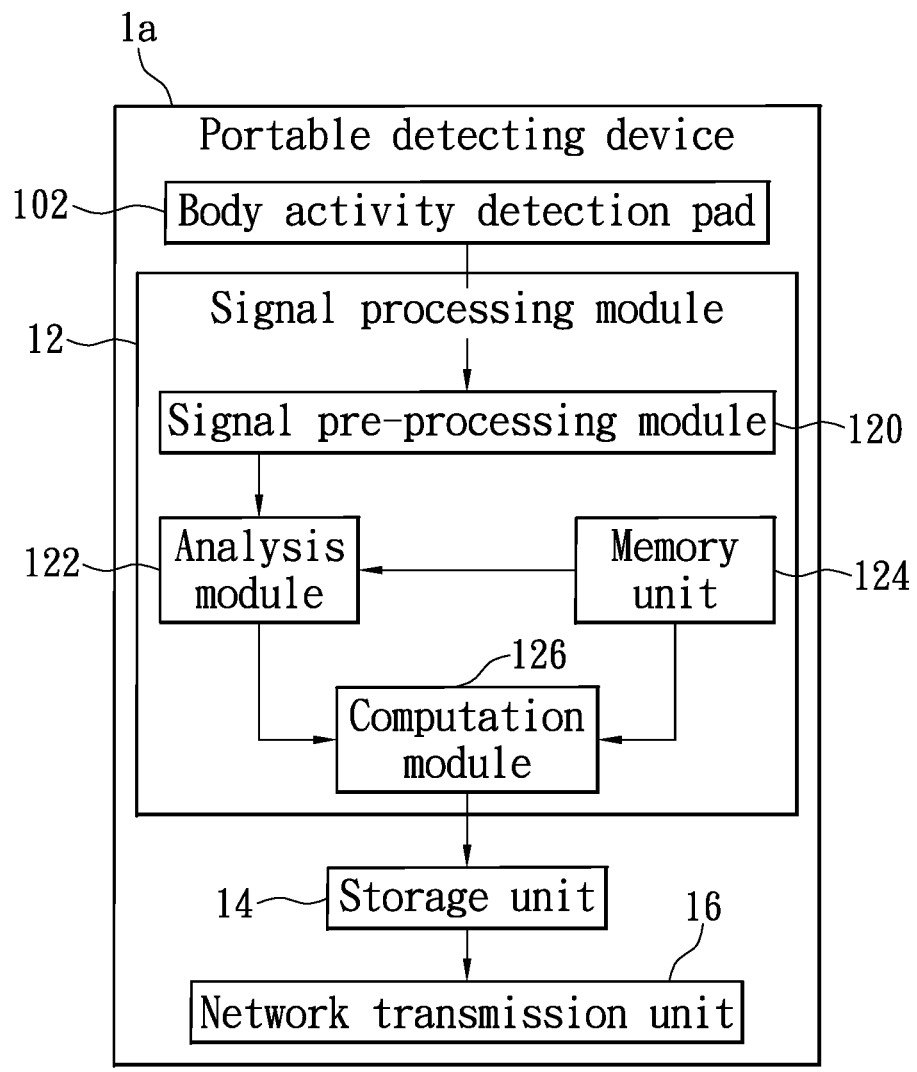
FIG. 3 is a block diagram of a portable detecting device of a sleep quality detection system in accordance with a preferred embodiment of the present invention.
Figure 4:
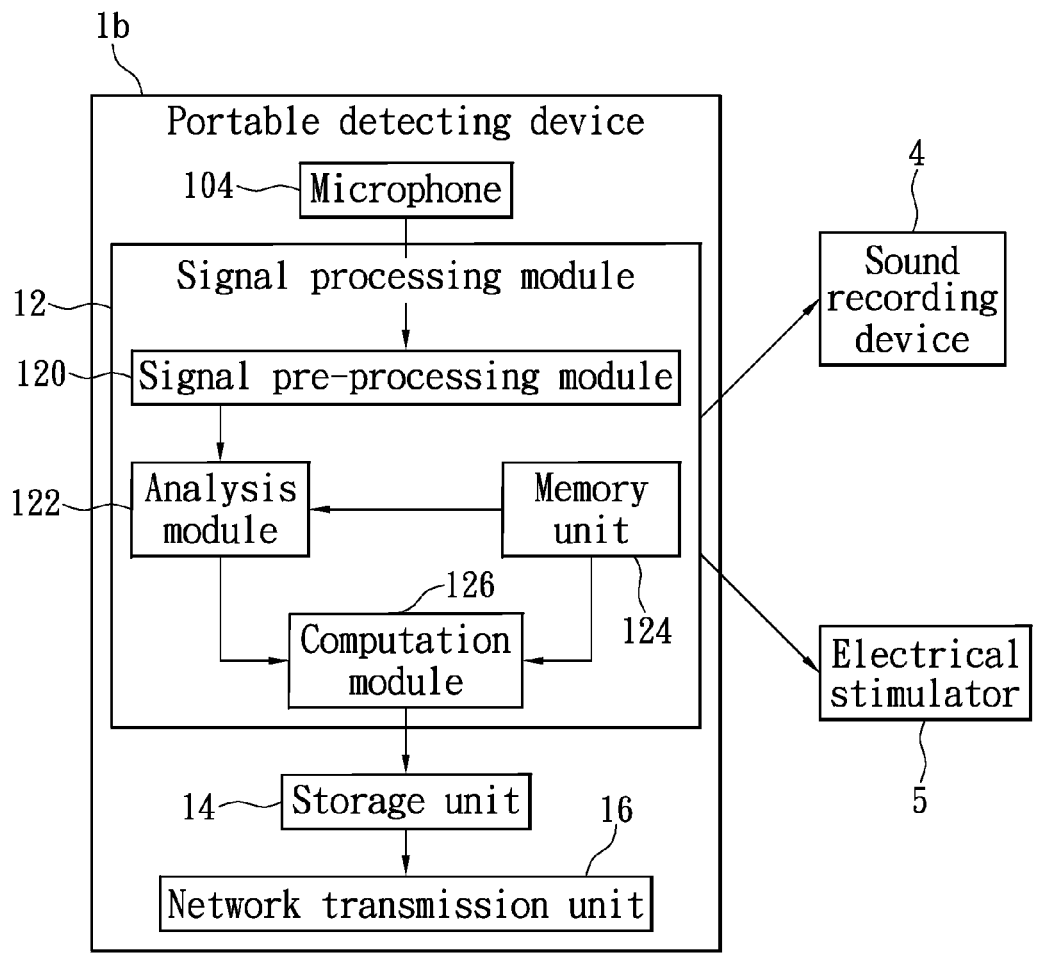
FIG. 4 is a block diagram of a portable detecting device of a sleep quality detection system in accordance with another preferred embodiment of the present invention.

With reference to FIGS. 3 and 4 for block diagrams of a portable detecting device of a sleep quality detection system in accordance with preferred embodiments of the present invention, FIG. 3 shows a state of the examinee's body activity while the examinee is sleeping. In a preferred embodiment, a body activity detection pad 102 of the portable detecting device 1a is provided for detecting the examinee's upper arm movement, body movement or leg movement to generate an upper arm activity signal, a body activity signal or a leg activity signal respectively. In addition, the body activity detection pad 102 of this embodiment can detect information such as the examinee's breathing frequency or body temperature.

In an example of detecting a body movement, a signal pre-processing module 120 digitizes, filters and samples the body activity signal generated by the body activity detection pad 102, and then an analysis module 122 analyzes variations of the slope of the body activity signal's waveform (from now on referred as 'slope variation') and reads a variation threshold such as 0.02 from a memory unit 124, and classifies the body activity signal according to the slope variation. A statistical value UAI is produced after the time greater than a threshold is counted in every minute, wherein the statistical value UAI represents the time (such as 3.5 seconds) of a specific body movement occurred in one minute.

The computation module 126 receives a statistical value BAI generated by the analysis module 122 and reads a computation equation from the memory unit 124 to compute the statistical value BAI. One of the equation is a weighted computation equation that decreases the significance of the activity signal as time passes, wherein the measurement of the passing time starts after the activity signal has been detected. In other words, the statistical value BAIT received by the computation module 126 is the time period of a body movement in the $i^{th}$ minute, and a statistical value BAIi-1 is collected in the previous minute, and a statistical value BAIi-2 is collected in the previous two minutes, and so forth, and the statistical values of a total of k minutes are compared. The longer the time taken for collecting the statistical value, the less is the weight given to the statistical value, and vice versa. The total sum is averaged to produce the weighted statistical value of a time period of a body movement occurred in the recent one minute. The statistical value LAI of a leg activity signal generated by the leg movement and the weighted statistical value of the time period of the leg movement are also computed as described above, and the same applies to the upper arm movement as well. Another example is taken for computing a weighted statistical value (wBAIi) of a body activity signal as follows:

$$wBAI_i = \sum_{n=1}^{k} BAI_{i-n+1} \cdot (k-n+1) / \sum_{n=1}^{k} n$$

The computation module 126 reads another sleep depth equation from the memory unit 124, and uses the sleep depth equation and the weighted statistical values of the upper arm activity signal and the leg activity signal to compute the examinee's sleep depth in the currently computed minute, and the sleep depth equation is given below:

SleepDepth=0.659-0.028·wBAI-0.026·wLAI where, wBAI is the weighted statistical value of a body activity signal; and wLAI is the weighted statistical value of a leg activity signal.

Figure 6A:
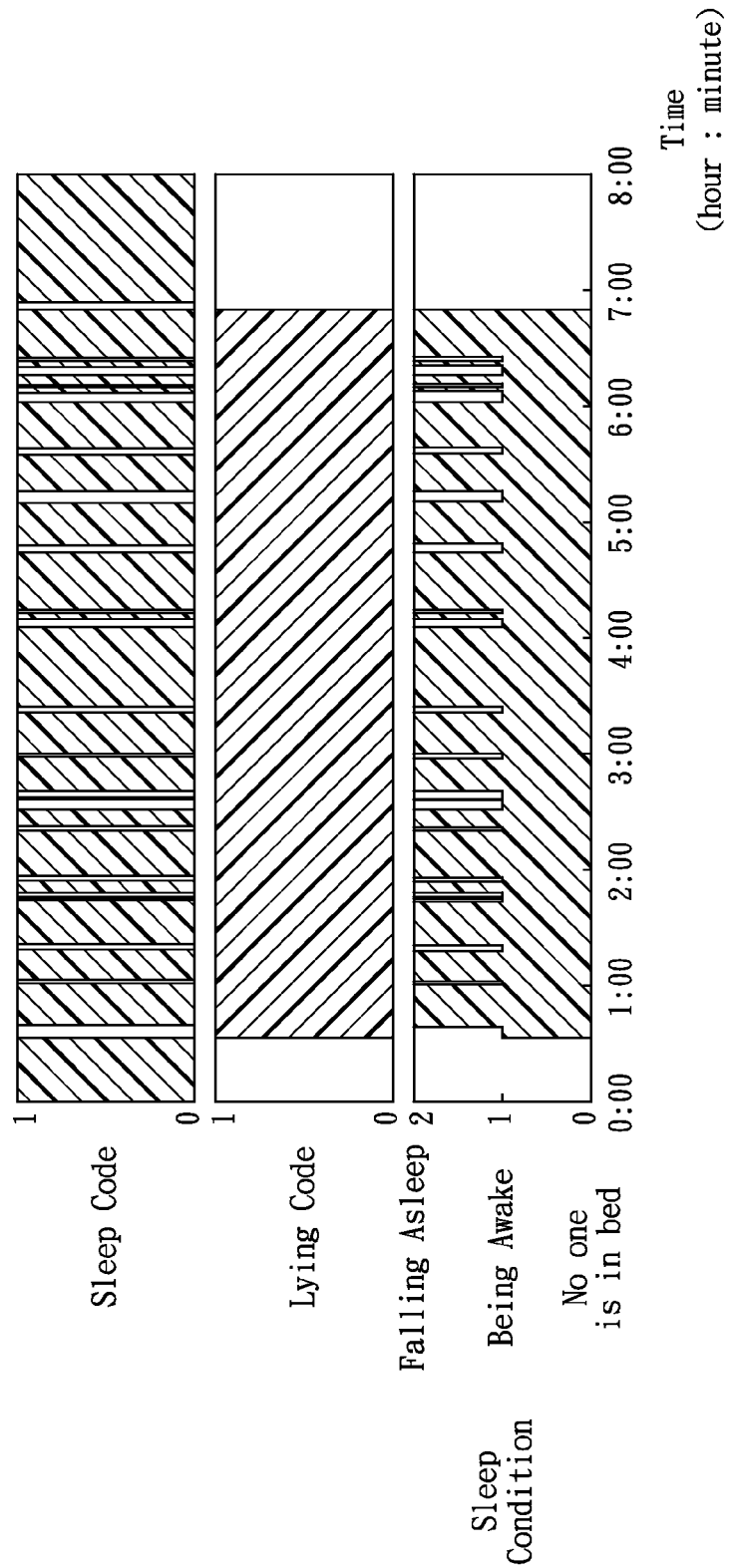
FIGS. 6A and 6B are schematic views of sleep quality information of a sleep quality detection system in accordance with a preferred embodiment of the present invention.

The computation module 126 computes the sleep depth of the examinee for every minute by the aforementioned equation, and compares the computed sleep depth with a sleep state index (which is the sleep depth threshold in this embodiment) recorded in the memory unit 124. The sleep depth is generally divided into two main types, wherein a value greater than the sleep depth threshold is "1", and a value smaller than the sleep depth threshold is "0". In the meantime, these values are used for comparison. Finally, sleep quality information is produced. In this embodiment, the sleep quality information refers to the examinee's sleep condition (as shown in FIG. 6A). If the examinee is lying in bed and the sleep depth is greater than the threshold, then the sleep condition is "Falling asleep". If the examinee is lying in bed, but the sleep depth is less than the threshold, then the sleep condition is "Being awake". If the sleep depth is less than the threshold and the examinee's index indicates that the examinee is not in bed, then the sleep condition is "No one is in bed".

Since the signal detector 10 of this embodiment is a body activity detection pad, the signal detector 10 can naturally and easily detect whether or not the examinee is lying in bed, in addition to the detection of the aforementioned activity signals.

With the foregoing analysis and computation, a complete set of sleep quality information can be obtained, so that the examinee's actual sleep condition such as whether the examinee sleeps soundly or wakes up frequently throughout the night can be observed, and the sleep condition is recorded in the storage unit 14. If it is necessary to examine the examinee's sleep quality information, the content stored in the storage unit 14 can be transmitted and retrieved by the network transmission module 16.

FIG. 4 shows a block diagram of a portable detecting device of a sleep quality detection system in accordance with another preferred embodiment of the present invention, this embodiment is used for detecting the examinee' snoring condition while the examinee is sleeping, and analyzing whether or not the examinee suffers from Obstructive Sleep Apnea Syndrome (OSAS).

The portable detecting device 1b of this embodiment uses a microphone 104 to detect and receive the examinee's snore while the examinee is sleeping and generate a snore signal. The signal pre-processing module 120 of the signal processing module 12 receives the snore signal and digitizes and filters noise to take samples, and eliminate any high-frequency signal exceeding the frequency defined by the snore from the snore signal to avoid the case of including irrelevant sounds into the analysis.

After receiving the filtered snore signal, the analysis module 122 analyzes a slope variation of the snore signal, reads a variation threshold of the slope recorded by the memory unit 124, classifies the snore signal into two main types according to the variation threshold, and collects the statistics. For example, if the slope is greater than the threshold, then the snore signal is classified as "1", and if the slope is smaller than the threshold, then the snore signal is classified as "0", and the statistics of the time periods exceeding the threshold are collected continuously, and the time period is classified as to whether or not it falls within the time during which snore is present. For example, if the time periods exceeding the threshold continuously fall within a range from 0.8 to 1.6 seconds, then it is classified as one snore. The foregoing method is used for determining whether or not the time period is for one snore, and selectively recording the time period in the memory unit 124 for the use by the analysis module 122. Finally, the frequency of snores per minute is counted to produce a snore frequency statistical value.

In this embodiment, the analysis module 122 analyzes the time interval and the frequency of snores occurred per minute, and divides the examinee's snore into a general snore and an intermittent snore according to the time interval between two snores. For example, if the time interval between two snore falls within a range from 10 seconds to 60 seconds, then the snore is considered as an intermittent snore, and if the time interval between two snores is less than 10 seconds, then the snore is considered as a general snore, and the frequency of intermittent snores per minute is counted to produce an intermittent snore frequency statistical value.

The computation module 126 computes an intermittent snore ratio (ISR) of snores occurred in one minute according to the snore frequency statistical value and the intermittent snore frequency statistical value. In addition, the computation module 126 reads a computation equation from the memory unit 124, and the computation equation is a weighted computation equation of significance of the snore signals decremented with time after the snore signals are detected. In other words, the computation module 126 compares the intermittent snore ratio ISRi in the recent minute with the intermittent snore ratio ISRi-1 of the previous minute, the intermittent snore ratio ISRi-2 of the previous two minutes, up to the intermittent snore ratio ISRi-k+1 of the previous k minutes. The longer the time of the intermittent snore ratio, the less is the weight, and vice versa. The total sum is averaged to produce the weighted statistical value of the intermittent snore ratio in the recent minute. For example, the weighted statistical value (wISRi) of the intermittent snore ratio occurred in recent five minutes is computed as follows:

$$wISR_i = \frac{5}{15} \cdot ISR_i + \frac{4}{15} \cdot ISR_{i-1} + \frac{3}{15} \cdot ISR_{i-2} + \frac{2}{15} \cdot ISR_{i-3} + \frac{1}{15} \cdot ISR_{i-4}$$

The larger the weighted statistical value (wISRi), the higher is the intermittent snore ratio of the examinee, and the higher is the probability for the examinee to suffer from Obstructive Sleep Apnea Syndrome (OSAS).

Figure 6B:
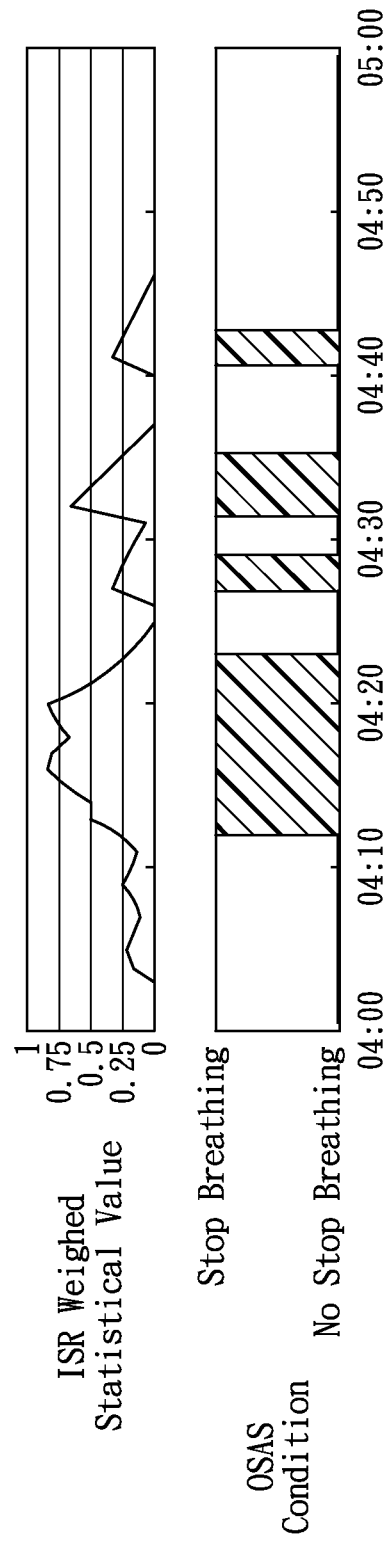

After the computation module 126 computes the weighted statistical value of the intermittent snore ratio, the result is compared with an intermittent snore ratio threshold recorded in the memory unit 124 to produce the examinee's sleep quality information relating to Obstructive Sleep Apnea Syndrome (OSAS). For example, if the weighted statistical value of the intermittent snore ratio is greater than 0.25, then the examinee is considered to suffer from "OSAS", and if the weighted statistical value of the intermittent snore ratio is smaller than 0.25, then the examinee is considered not to suffer from "OSAS" as shown in FIG. 6B. Thus, this method allows the examinee to know whether or not there is any OSAS symptom occurred while the examinee is sleeping and determine whether or not to seek for medical treatment according to the information. Finally, the detected snore signal and sleep quality information are recorded in the storage unit 14, and selectively transmitted to the network transmission unit 16 via the network 6, if needed.

This embodiment further comprises a sound recording device 4 and an electrical stimulator 5 coupled to the signal processing module 12. The sound recording device 4 records and provides contents of snores produced by the examinee as a reference information for a medical treatment according to the instruction of the signal processing module 12. The electrical stimulator 5 such as a transcutaneous electrical nerve stimulator produces a slight electric current to stimulate the examinee if the examinee is diagnosed to suffer from OSAS and helps the examinee to restore a normal breathing and saves the examinee from the danger of a possible OSAS.

From the embodiment as described above, we know that the present invention can detect the examinee's sleep information continuously for a long term without affecting the examinee's sleep, and recording objective and accurate information which is absolutely helpful to the diagnosis of the examinee's sleep disorder.

In the foregoing embodiment, the body activity and the snore are detected separately for the simplicity of illustrating the present invention, but they can be combined in actual implementation as well. The invention has the function of detecting the body activity and snore simultaneously to provide complete sleep quality information detected by the portable detecting device 1.

Figure 5A:
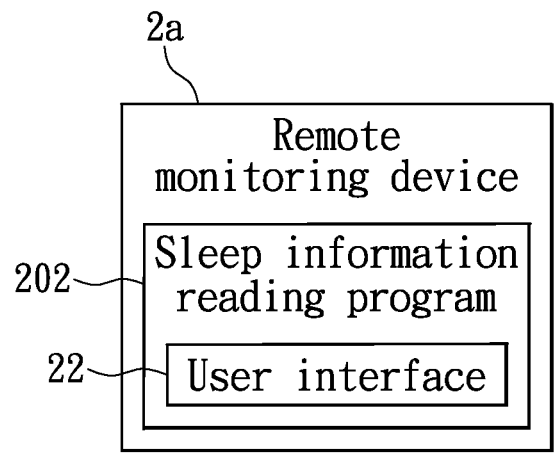
FIGS. 5A and 5B are block diagrams of a remote monitoring device of a sleep quality detection system in accordance with a preferred embodiment of the present invention.
Figure 5B:
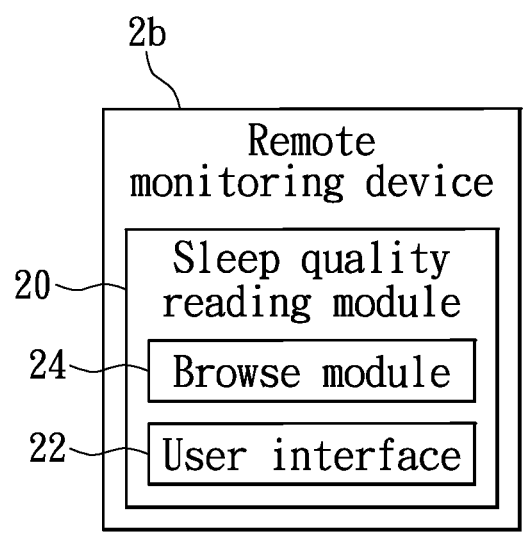

The remote monitoring device 2 reads the activity signal and the sleep quality information stored in the storage unit 14 of the portable detecting device 1 via the network 6. With reference to FIGS. 5A and 5B for block diagrams of a remote monitoring device of a sleep quality detection system in accordance with preferred embodiments of the present invention, FIG. 5A shows a remote monitoring device 2a comprising a sleep information reading program 202, which is a VB application program and provides a user interface 22, and FIG. 5B shows another preferred embodiment of a sleep quality reading module 20 of a remote monitoring device 2b, comprising a browse module 24 such as a webpage browser for accessing an application server system (not shown in the figure) to obtain the user interface 22.

The remote monitoring device 2a or 2b receives a connection instruction for connecting the portable detecting device 1 through the user interface 22, such as entering a network address of the portable detecting device 1, connecting the portable detecting device 1 via a distributed network according to the connection instruction, and reading the sleep quality information (such as the aforementioned sleep condition information or Obstructive Sleep Apnea Syndrome (OSAS) information collected while the examinee is sleeping) stored in the storage unit 14, and displaying the sleep quality information on the user interface 22 timely for medical and healthcare professionals to monitor and control the sleep information or reading history information recorded in the storage unit 14 back to the user interface 22 according to another operation instruction received by the user interface 22 after the portable detecting device 1 is connected, so that medical and healthcare professionals can observe the examinee's past sleep information and take necessary actions.

From the description above, we know that a sleep quality detection system is constructed by a distributed structure, so that both of the examinee and medical and healthcare professionals can obtain the detected and monitored information by the most convenient method. The invention reduces the examinee's psychological and monetary burdens and provides accurate successive data which are very helpful to related medial professionals for diagnosing and curing the examinee's sleep disorder.

Figure 7:
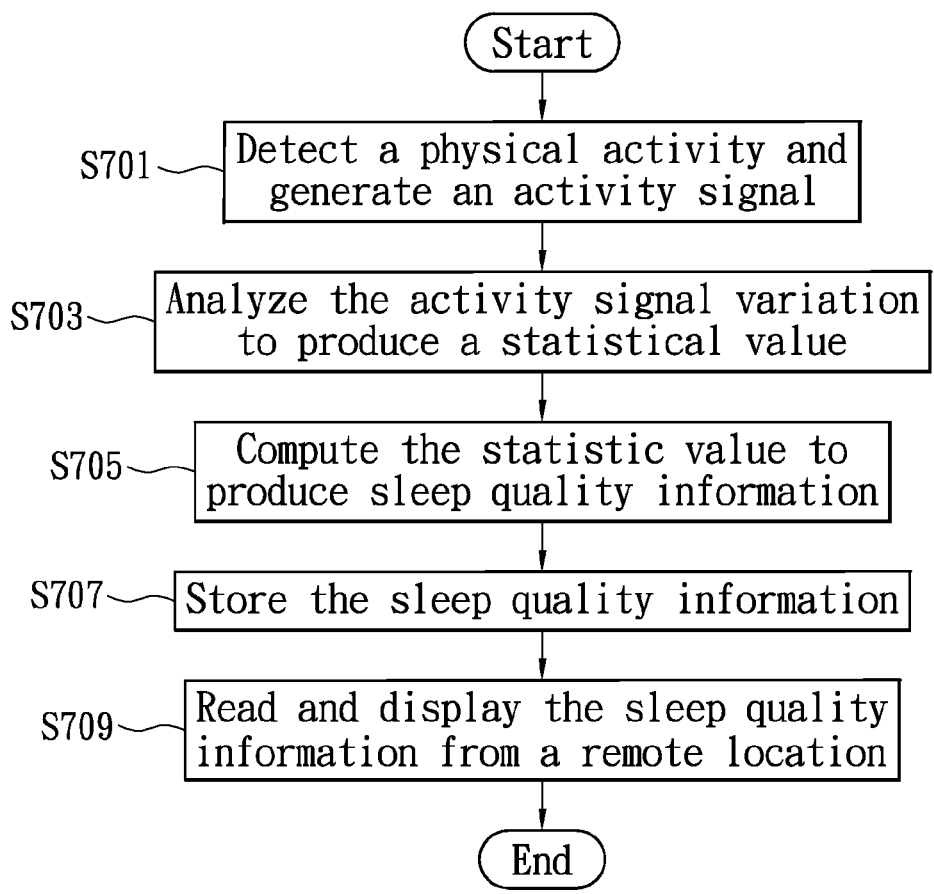
FIG. 7 is a flow chart of a sleep quality detection method in accordance with a preferred embodiment of the present invention.

With reference to FIG. 7 for a flow chart of a sleep quality detection method in accordance with a preferred embodiment of the present invention, the method comprises the following steps: A signal detector 10 detects the examinee's physical activity while the examinee is sleeping and generates an activity signal (S701). An analysis module 122 analyzes the activity signal varied with time, and classifies and collects the statistics of the activity signals to produce a statistical value (S703). A computation module 126 computes the statistical value and compares the result with a sleep state index to produce sleep quality information (S705). The sleep quality information is stored in a storage unit 14 (S707). A sleep quality reading module 20 is provided for reading the sleep quality information from a remote location via a network 6 and displaying the sleep quality information on a user interface 22 of the remote monitoring device 20 (S709). Therefore, medical and healthcare professionals can monitor and observe the examinee's sleep quality information in the long term from the remote location, without disturbing the examinee's sleep, and further analyze or evaluate the examinee's sleep quality according to the observed sleep quality information, and cure the examinee's sleep disorder.

Before the activity signal is analyzed, a signal pre-processing module 120 digitizes and filters noises of the detected activity signal and takes samples for the analysis. The step for the sleep quality reading module 20 to read the sleep quality information further comprises the steps of providing a browse module 24 to access an application server system to obtain the user interface 22, and connecting the user interface 22 to obtain the sleep quality information after a connection instruction is received.

The method of this embodiment further comprises the steps of recording the activity signal in the storage unit 14; and providing a memory unit 124 for recording a variation threshold provided for the analysis module 122 to classify the activity signal according to its variation, and also recording a computation equation for computing a statistical value by the computation module 126, and recording a sleep state index which is compared with the computed result and provided for the operation of the aforementioned steps. The computation equation includes a weighted computation equation which is a computation equation of significance of the activity signal decremented with time after the activity signal is detected, so that the level of physical activity represented by the most recently detected activity signal becomes more significant. This embodiment further comprises the steps of: providing an alarm receiving unit 3 such as a mobile communication device or an email; receiving an alarm notice and transmitting the alarm notice to a medical or healthcare professional via the network 6 for taking an emergency action if an abnormal activity signal of the examinee is detected.

Figure 8:
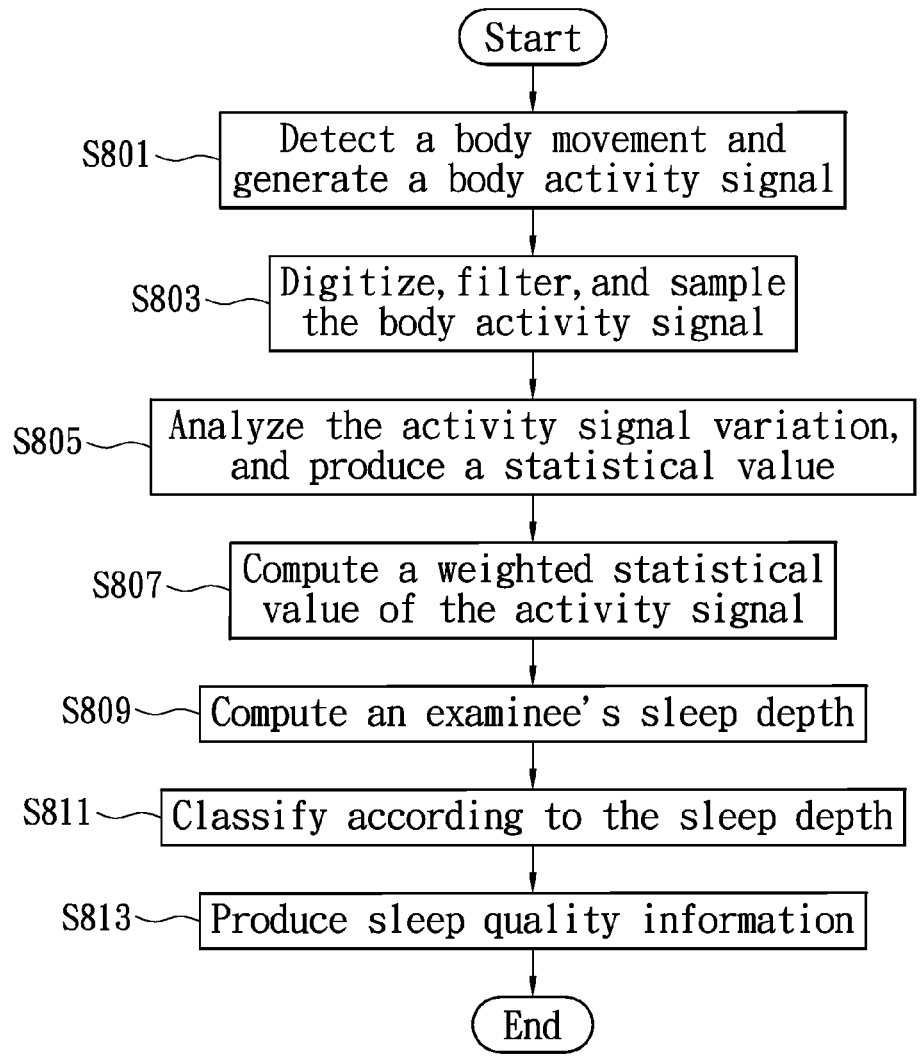
FIG. 8 is a flow chart of detecting a physical activity in a sleep quality detection method in accordance with a preferred embodiment of the present invention.

With reference to FIG. 8 for a flow chart of detecting a physical activity in a sleep quality detection method in accordance with a preferred embodiment of the present invention, the method comprises the steps of: providing a body activity detection pad 102 to detect the examinee's upper arm movement, body movement or leg movement and generate an upper arm activity signal, a body activity signal or a leg activity signal respectively (S801); providing a signal pre-processing module 120 to digitize, filter and sample the activity signal (S803); analyzing a slope variation of the activity signal varied with time by an analysis module 122 to classify the activity signal according to the slope variation and a variation threshold recorded in the memory unit 124 and collect the statistics of the time greater than the threshold in a minute, and generate a statistical value of the time period of the body, leg, or upper arm movement (S805). A computation module 126 reads a weighted computation equation from the memory unit 124 and computes the weighted statistical value of the time period of the upper arm movement and the time period of the leg movement (S807), and reads a sleep depth computation equation, such that the sleep depth computation equation and the weighted statistical values of the upper arm activity signal and the leg activity signal can be used for computing the examinee's sleep depth in the recent minute (S809). The sleep depth threshold is compared and divided into two types: a sleep depth greater than the threshold and a sleep depth smaller than the threshold (S811). Finally, an index indicating whether or not the examinee is lying in bed is provided for producing sleep quality information, and the examinee's sleep condition such as "falling asleep", "being awake" and "no one is in bed" is displayed (S813). The detailed computing procedure of the computation module 126 is illustrated in FIG. 3. The remote monitoring device 20 reads the examinee's sleep condition while the examinee is sleeping and provides the sleep condition for the examinee to determine whether or not the examinee has an insomnia problem.

Figure 9:
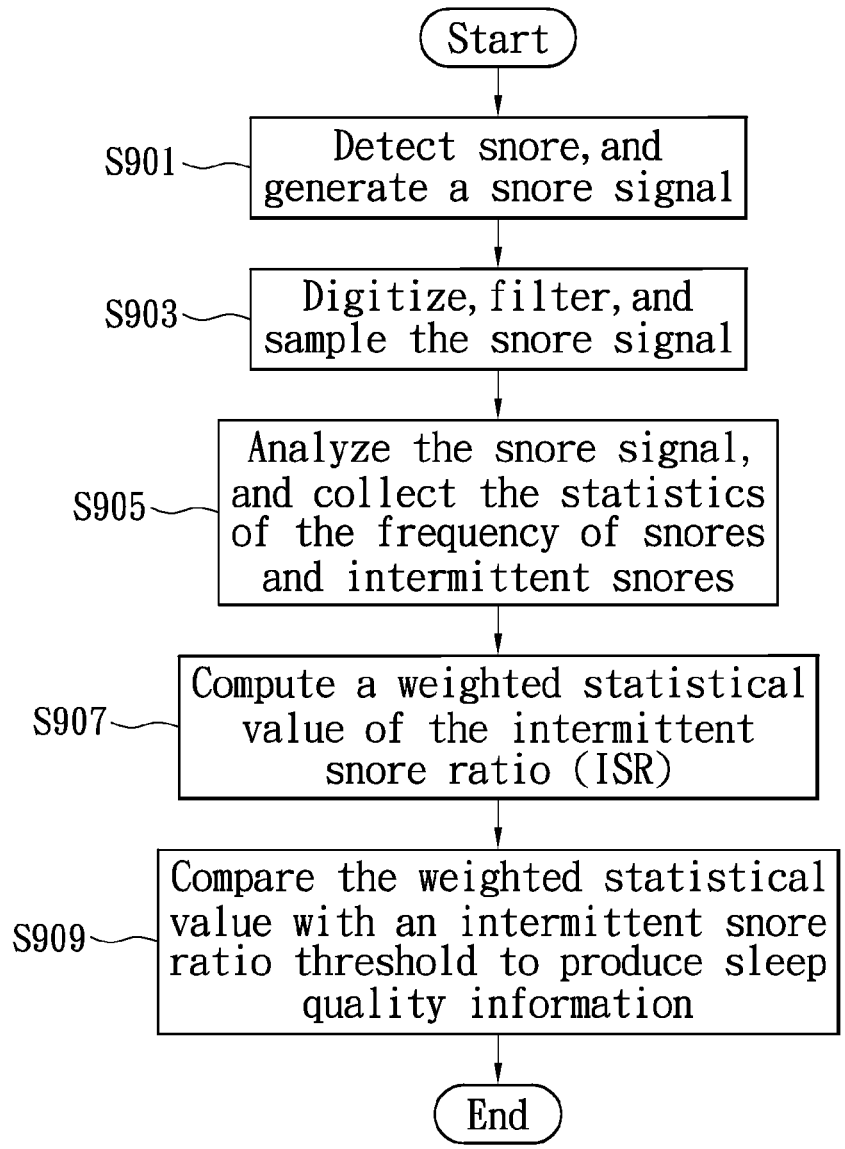
FIG. 9 is a flow chart of detecting snore in a sleep quality detection method in accordance with a preferred embodiment of the present invention.

With reference to FIG. 9 for a flow chart of detecting snore in a sleep quality detection method in accordance with a preferred embodiment of the present invention, the method comprises the steps of: providing a microphone 104 for detecting snore produced by the examinee while the examinee is sleeping, and generating a snore signal (S901); digitizing, filtering the portion with a too-high frequency, and sampling the snore signal by a signal pre-processing module 120 (S903); analyzing a slope variation of the snore signal varied with time by an analysis module 122, and classifying the snore signal according to the slope variation and the variation threshold recorded in the memory unit 124 and collecting the statistics of the frequency of intermittent snores occurred in a minute (S905), wherein the detailed analysis procedure is illustrated in FIG. 4.

The computation module 126 computes a statistical value produced by the analysis module 122 according to a computation equation stored in the memory unit 124, and uses the computation equation as disclosed in FIG. 4 to produce a weighted statistical value of the intermittent snore ratio (ISR) (S907), wherein the larger the weighted statistical value, the higher is the probability for the examinee to suffer from Obstructive Sleep Apnea Syndrome (OSAS), and then the intermittent snore ratio threshold recorded in the memory unit 124 is used for comparing the computed weighted statistical value to produce sleep quality information (S909), and a weighted statistical value greater than the threshold is recorded as "OSAS", and a weighted statistical value greater than the threshold is recorded as "No OSAS", and these values are provided for medical and healthcare professionals to monitor the examinee's condition.

In addition, the present invention also records the examinee's snores, uses a sound recording device 4 to record the examinee's snores while the examinee is sleeping, and provides an electrical stimulator 5 for transmitting a slight current to stimulate an examine to resume a normal breathing and avoid the danger of OSAS when an abnormal snore signal of the examinee is detected.

In summation of the description of the aforementioned preferred embodiments, the present invention provides a natural and comfortable way of detecting the examinee's sleep information in an environment familiar to the examinee. The present invention not only saves the trouble of going to a specific hospital or clinic, but also avoids disturbing the examinee during the processes of performing the detection and connecting information by the portable detecting device, so that the examinee can take a test without a burden. The invention detects and obtains more accurate information, and also saves the cost for the examinee to go to a hospital or a clinic to take the test. More importantly, medical and healthcare professionals can observe the examinee's sleep condition anytime and read the examinee's sleep information to determine and make further diagnoses and treatment, so as to enhance the accuracy of analyzing the sleep disorder symptoms and the efficiency of curing the examinee's sleep disorder.

Although the present invention has been described with reference to the preferred embodiments thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A remote sleep quality detecting method, comprising the steps of:

providing a signal detector for continuously detecting a physical activity of an examinee while the examinee is sleeping, and generating an activity signal;

analyzing changes of the activity signal varied with time, and producing a statistical value according to variation classification and statistics of the activity signal;

computing the statistical value, and comparing a computed result with at least one sleep state index to produce sleep quality information;

recording the sleep quality information in a storage unit;

providing a remote monitoring device, and displaying the sleep quality information read via a network at a user interface;

recording the activity signal in the storage unit; and providing a memory unit for storing a variation threshold, at least one computation equation and the sleep state index, classifying the activity signal according to the classification of the variation threshold, and computing the statistical value according to the computation equation;

whereby the sleep quality information of the examinee can be observed at a remote location for a long term, and the sleep quality of the examinee can be analyzed further according to the sleep quality information;

wherein the computation equation is a weighted computation equation according to the level of significance of the activity signal decreasing with time after the detection takes place.

2. The remote sleep quality detecting method of claim 1, further comprising a procedure before the step of analyzing the activity signal, and the procedure comprising the steps of:

digitizing and filtering the activity signal; and sampling the activity signal.

3. The remote sleep quality detecting method of claim 1, further comprising a procedure during the step of detecting a physical activity by the signal detector while the examinee is sleeping, and the procedure comprising the steps of:

the signal detector detecting body activity while the examinee is sleeping; and generating a body activity signal.

4. The remote sleep quality detecting method of claim 3, wherein the signal detector is a body activity detection pad, and the body activity signal is an upper arm activity signal, a body activity signal or a leg activity signal.

5. The remote sleep quality detecting method of claim 1, further comprising a procedure during the step of reading the sleep quality information by the sleep quality reading module, consisting of:

accessing an application server system from a browse unit for providing the user interface.

6. The remote sleep quality detecting method of claim 1, further comprising the step of providing an alarm receiving unit for receiving an alarm notice when an occurrence of an abnormal activity signal is detected.

7. The remote sleep quality detecting method of claim 6, wherein the alarm receiving unit is a mobile communication device or email.

* * * * *